United States Patent [19]

Seifert

[11] Patent Number: 4,984,381
[45] Date of Patent: Jan. 15, 1991

[54] FIREARM WEAR ANALYSIS

[75] Inventor: William W. Seifert, Wellesley Hills, Mass.

[73] Assignee: Institute Guilfoyle, Belmont, Mass.

[21] Appl. No.: 325,296

[22] Filed: Mar. 17, 1989

[51] Int. Cl.$^5$ ............................................. F41C 31/04
[52] U.S. Cl. ...................................... 42/1.01; 42/106; 73/167
[58] Field of Search .................... 42/1.01, 106; 89/1.1; 73/167

[56] References Cited

U.S. PATENT DOCUMENTS

| | | | |
|---|---|---|---|
| 3,932,748 | 1/1976 | Schmitz | 73/167 |
| 4,047,814 | 9/1977 | Westcott | 356/70 |
| 4,448,887 | 5/1984 | Kauffman et al. | 73/64 |
| 4,532,815 | 8/1985 | Gee et al. | 73/167 |

Primary Examiner—Charles T. Jordan
Attorney, Agent, or Firm—Nutter, McClennen & Fish

[57] ABSTRACT

A technique for evaluation of various firearm and projectile wear parameters. A debris collector constructed in accordance with the invention includes a receptacle coated with a collecting medium capable of trapping the particles exhausted from a firearm. The receptacle is formed of a fairly ductile material, such as metal foil, so that it is easily penetrated when a projectile is fired into the apparatus. The preferred collecting medium is a polymer blend of white petrolatum and paraffin wax, which exhibits ideal receptivity to impinging particles, while retaining excellent solubility, temperature stability, and shelf life. An appropriate container serves to support and enclose the collecting medium.

The collecting medium is then removed from the receptacle for further analysis. It is liquefied by dissolving it in a suitable carrier fluid such as by applying heat or a solvent. The result is a clear liquid containing suspended wear particles. The clear liquid can be visually inspected. However, other techniques such as ferrography are preferred.

19 Claims, 4 Drawing Sheets

FIREARM WEAR ANALYSIS

FIELD OF THE INVENTION

This invention relates generally to firearm testing, and particularly to a technique for collecting and analyzing the debris produced as a projectile travels down a firearm barrel, thus enabling evaluation of various firearm wear parameters.

BACKGROUND OF THE INVENTION

When a firearm is fired, minute particles are invariably worn away, from both the firearm barrel and the projectile. Some particles will adhere to the barrel, and the rest are expelled with the projectile.

For hundreds of years lead has been the most popular material for projectiles. However, in recent years, the public has become increasingly vocal about the health problems caused by poisons such as lead. Law enforcement officials and others who frequently use practice ranges run the greatest risk of direct exposure to the lead particles produced by the use of lead shot. It is thus desirable to reduce the number of particles worn from the projectile as it is expelled.

Particles worn from the barrel have historically presented a problem which is primarily manifested as loss of accuracy after many firings. Excessive wear resulting from many firings or from the use of unauthorized propellant, such as in muzzle loaders, can also present a safety hazard if failure of the forcing cone or barrel occurs.

These health and safety problems are related in that their eventual solution depends upon determining the number and type of particles expelled from a firearm. For example, analysis of the number and type of particles expelled after a single shot can be used to determine the effectiveness of treating the barrel or the projectile, such as by cladding. Statistics collected on the number and type of particles generated during a series of test firings can be used to predict the longevity of different barrel and shot material combinations.

Several techniques for analyzing barrel wear are presently in use. These include fluoroscopic examination, observation of decreasing accuracy, precision gauging, and other elaborate methods. However, because of their expense and logistic complexity, these known techniques do not easily lend themselves to obtaining relative data over many firings.

One wear analysis technique, developed for evaluating the condition of oil lubricated engines, does provide data without these disadvantages. It is based on direct examination of the quantity, size, and rate of increase of contaminants in the lubricating oil. See, for example, U.S. Pat. No. 4,448,887 issued to Kauffman, et al. Examination can be accomplished in several ways, such as visually, or by spectroscopy. However, a method known as ferrography is a particularly convenient and inexpensive way to determine these parameters. See U.S. Pat. No. 4,047,814 issued in September, 1977 to Westcott.

If ferrography could be applied to accurately determine the quantity, size, and type of wear particles from a firearm blast, an important tool for appraising various combinations of projectiles and methods of reducing barrel wear would exist. Information about the composition of the wear particles could also be used to interpret the nature of the wear process.

SUMMARY OF THE INVENTION

A general object of this invention is to provide a technique for collecting the debris produced as a projectile travels down the barrel of a firearm. The technique should be inexpensive to administer, and minimize the need for large numbers of test firings. It should be adapted to facilitate later analysis of the wear particles, particularly after they have been stored or shipped to a remote laboratory.

Briefly, a debris collector constructed in accordance with the invention includes a receptacle coated with a collecting medium. The medium is any substance capable of trapping the particles exhausted from a firearm. The receptacle must be formed of a fairly ductile material, such as metal foil, so that it can be easily punctured when a projectile is fired into the apparatus, while still maintaining the ability to collect as many particles as possible.

A preferred collecting medium is a polymer blend of white petrolatum and paraffin wax. This composition exhibits ideal receptivity to impinging particles, while retaining excellent solubility, temperature stability, and shelf life.

An appropriate container supports and retains the receptacle and medium. Covers may be fitted to the container to protect the contents before and after testing. A hole is formed near the center of a bottom surface of the container to allow the projectile to pass through.

A test is performed by placing the collecting medium a short distance in front of the firearm barrel after removing the covers. When the firearm is fired, most of the small particles worn from the projectile barrel are deposited in the medium, held in place by the receptacle and container.

After the gun is fired, the collecting medium is removed from the receptacle for analysis. The medium is first liquefied by heating it and then dissolved with a suitable carrier such as petroleum-based motor oil. A sample of the dissolved medium and carrier is then further diluted by mixing it with a solvent such as tetrachloroethylene. A clear liquid containing the wear particles in suspension results. A ferrogram is now prepared by running this liquid over a microscope slide located in a magnetic field. Magnetic, as well as paramagnetic and even diamagnetic, particles in the liquid are thus retained on the slide, and organized by size and type. Thus, in the present application, spheres of steel from the barrel, chunks of lead from the shot, and even bits of propellant are evident from microscopic examination of the ferrographic slide.

Comparison of ferrograms from individual test firings can be used to determine which barrel and shot combinations produce the least amount of particles. The results from several samples taken over a sequence of firings can be used to develop statistics on the life of the barrel. As with engine analysis, wear particles are often observed to be fairly large when a firearm barrel is new. The particles then get smaller for quite some time, but then abruptly become larger again before a catastrophic failure.

For testing large caliber firearms, similar methods appropriate for the larger scale of parameters may be applied.

The invention provides a convenient, accurate, and inexpensive way to determine how many and what kind of particles are emitted by a firearm, thereby facilitating the evaluation of firearms design parameters.

BRIEF DESCRIPTION OF THE DRAWINGS

This invention is pointed out with particularity in the appended claims. The above and further advantages of the invention may be better understood by referring to the following description in conjunction with the accompanying drawings, in which:

DETAILED DESCRIPTION OF AN ILLUSTRATIVE EMBODIMENT

Figure 1:
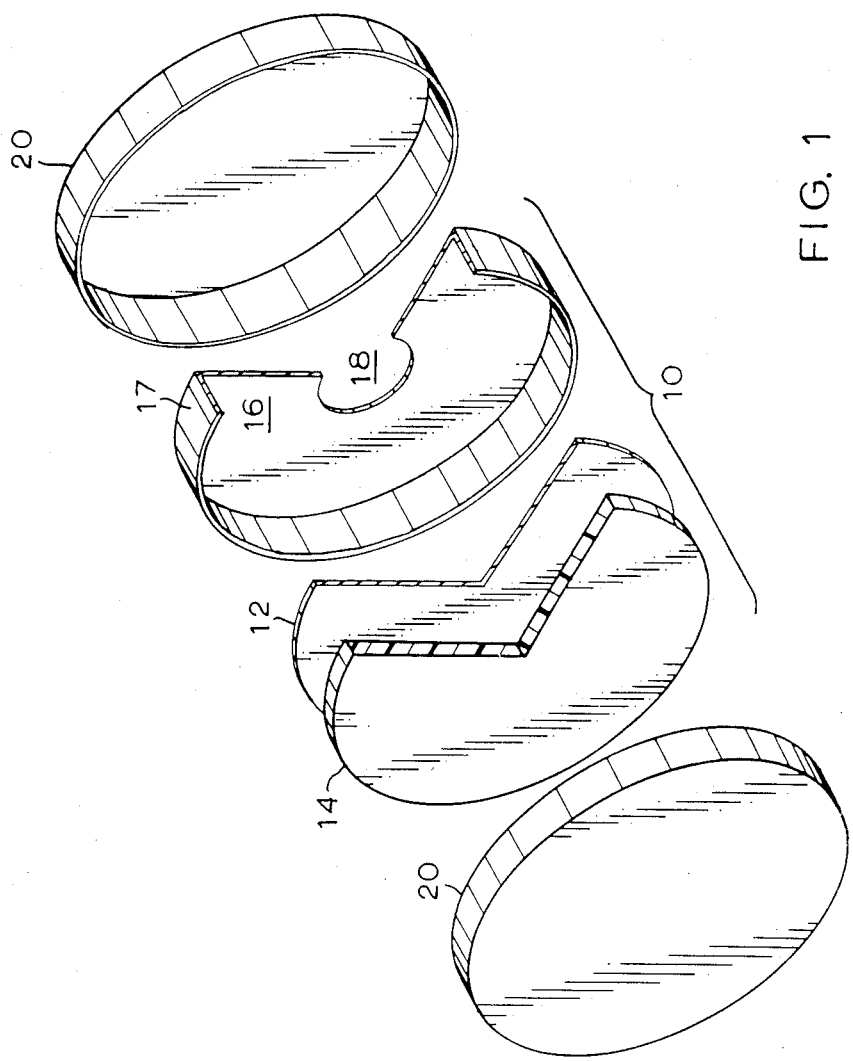
FIG. 1 is an isometric, partially cut away view of a firearm debris collector constructed in accordance with the invention.

Referring now to FIG. 1 more particularly, there is shown a firearm debris collector 10 constructed in accordance with the invention. The collector 10 includes a receptacle 12, a particle collecting matrix 14, and a container 16.

Receptacle 12 is a disk which is sufficiently thin and pliable to easily tear or bend away when struck by a projectile, but sufficiently resilient to support the matrix 14 at the point of projectile impact. Metal foil is the ideal material for receptacle 12. Although other shapes can be used, the disk is most efficient for collecting debris emitted from a circular barrel, as that tends to disperse particles uniformly in all directions around a central axis.

Matrix 14, disposed on an outer surface of the receptacle 12, is a medium specifically formulated for catching the high velocity impinging particles. Matrix 14 exhibits good solubility to facilitate later separation of the particles. It is stable over a range of temperature and humidity conditions, to enable storage of collector 10 for extended periods of time. Finally, the medium chosen for matrix 14 is also easy to later remove from the receptacle 12 such as by scraping.

Although a wide range of materials and formulation are satisfactory for the matrix 14 the preferred formulation is a blend of 70% United States Petroleum (U.S.P.) grade white petroleum jelly and 30% refined paraffin wax. This formulation is particularly adapted to facilitate later particle analysis by ferrography. However, matrix 14 is also quite advantageous as a collecting medium even when other analysis techniques such as spectroscopy are used.

The container 16 is formed of a material sufficient to house both the receptacle 12 and matrix 14, both during storage as well as while the collector 10 is impinged by firing debris. Aluminum or heavy gauge plastic are best. The receptacle 12 is fastened to the container 16 such as by cementing. A circular lip 17 may also be formed around the periphery of container 16 to assist the retaining function.

A hole 18 is preferably formed in the bottom surface of container 16 to allow the emitted projectile (not shown in FIG. 1) to pass through the receptacle 12 and matrix 14 with minimum interference.

Receptacle 12, matrix 14, and container 16 are large enough to collect most of the debris emitted from a point-blank shot. For a five inch diameter matrix, a distance of four to sixteen inches from the end of the muzzle to the matrix is sufficient for standard caliber rifles and handguns.

Covers 20 should be fitted over container 16 during shipping and storage to protect the contents. By so covering for shipment, the firearm can be discharged at a firing range remote from the laboratory where matrix 14 is analyzed.

Figure 2:
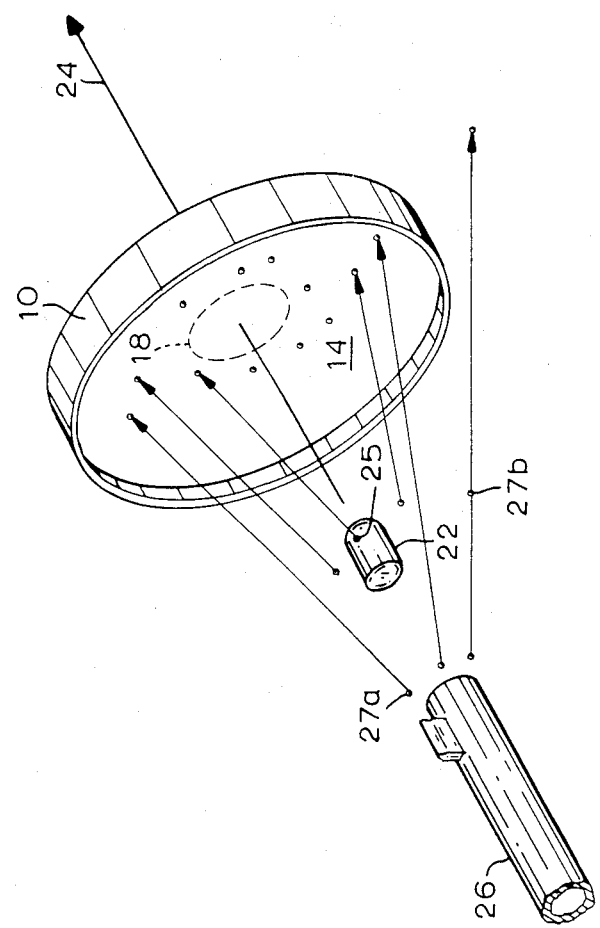
FIG. 2 shows how the collector is used.

FIG. 2 shows how collector 10 collects the debris emitted when a projectile 22 is fired along a path 24 from a firearm 26. Covers 20 are first removed, and the firearm 26 is positioned adjacent the collector 10, with the matrix 14 facing the barrel end of the firearm 26. The distance between them is preferably a suitable point blank range, (such as a few inches when the firearm 26 to be tested is a pistol). Firearm 26 is then aimed and fired so that projectile 22 travels along a path 24 passing through or near the hole 18 formed in container 16. As firearm 26 is fired, debris such as a projectile particle 25 and firearm particle 27a are emitted and then impact the collector 10, and are retained by matrix 14. Other particles, such as firearm particle 27b, will miss the collector 10.

Figure 3:
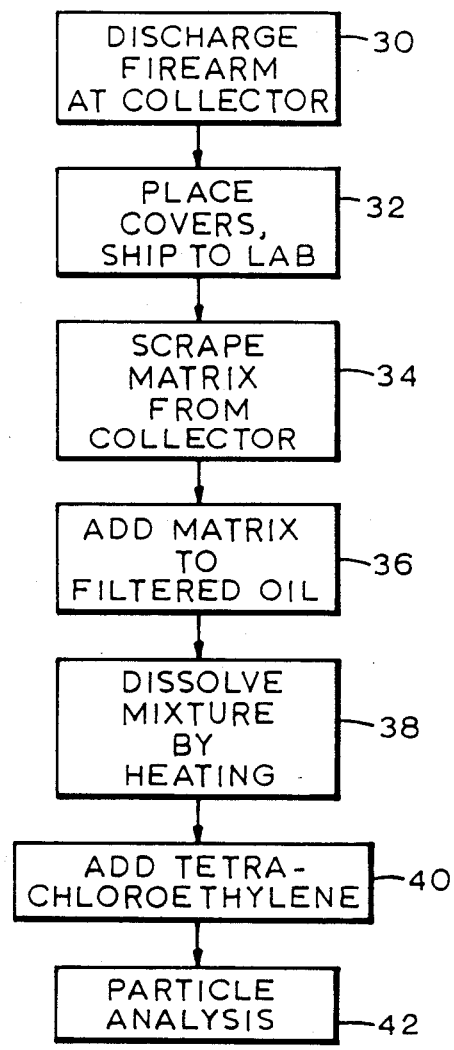
FIG. 3 is a sequence of steps performed to prepare the debris collected for analysis.

FIG. 3 depicts the sequence of steps performed in the process of preparing the collected debris for analysis. After the initial step 30 of discharging the firearm depicted in FIG. 2, the covers 20 are placed over the collector 10 for protection during shipment, as necessary, in step 32.

Upon arrival at the laboratory, after the covers are removed, the matrix 14 is scraped from collector 10 in step 34. The test administrator may choose to scrape all of matrix 14 or just a portion. It is preferable during a sequence of related tests to endeavor to always scrape only the matrix 14 located inside a particular radius about the hole 18. This not only is where most of the debris is concentrated, but also insures that debris is collected from an area of consistent size from test to test.

Next, in step 36, the scraped-away matrix 14 is mixed with a suitable carrier. If ferrography is to be used as an analysis technique, Society of Automotive Engineers (S.A.E.) weight 10W40 motor oil is appropriate. Matrix 14 will dissolve in the motor oil somewhat at room temperature, but complete dissolving is insured by then heating the carrier/matrix mixture slightly, such as to 150° F. (Fahrenheit), in step 38. Only enough carrier to cover the matrix 14 needs to be added; this is usually an approximately one to one mixture by volume.

As a last sample preparation step 40, a solvent such as tetrachloroethylene is mixed with the carrier and matrix to further insure the complete separation of the particles from the matrix 14. At least one part tetrachloroethylene to one part carrier/matrix mixture is typically necessary. The result is a clear liquid in which the particles are suspended.

Particle analysis then occurs in step 42. Exact chemical analyses such as spectroscopy might be used to determine the composition of the particles. However, ferrography is the preferred technique here. It is simple and convenient to administer.

The details of administering ferrographic tests are well known. A sample of the fluid to be analyzed is fed to an entry position above the top of an inclined substrate disposed in a magnetic field. The fluid is caused to travel along the slide, and metallic particles are thus retained on the substrate by the magnetic field. The retained particles are distributed along the substrate at varying distances from the entry point, depending upon their size, shape, and magnetic susceptability. For more details of the ferrography process, see U.S. Pat. No. 4,047,814 issued to Westcott.

In the present application, it has been discovered that spheres of steel from the barrel, chunks of lead from the shot, and even particles of propellant are evident upon microscopic examination of the ferrographic slide. That is, even slightly para-magnetic particles such as unburned powder are evident on the ferrographic slide, since they are also captured by the high-gradient magnetic field. It is seen, then that collector 10 provides a convenient, accurate, and inexpensive way to determine how many and what kind of particles are emitted by a firearm. Comparison of the types of particles emitted even in a single test firing can give valuable insight into which barrel and shot combinations produce the smallest number of projectile particles.

As with engine wear analysis, particles emitted from a firearm have been found to follow a predictable pattern over time. Specifically, relatively large barrel particles are emitted when the firearm is new. The barrel particles are then observed to be quite a bit smaller over the course of many firings. Finally, a noticeable increase in size is quite evident as severe deterioration or failure of the barrel approaches. Thus, the results of several tests taken from a sequence of firings can be used to develop statistics for the life of the barrel. The technique is also potentially useful as evidence in criminal proceedings to correlate the debris collected from a firearm with that collected from a victim's clothing.

Figure 4:
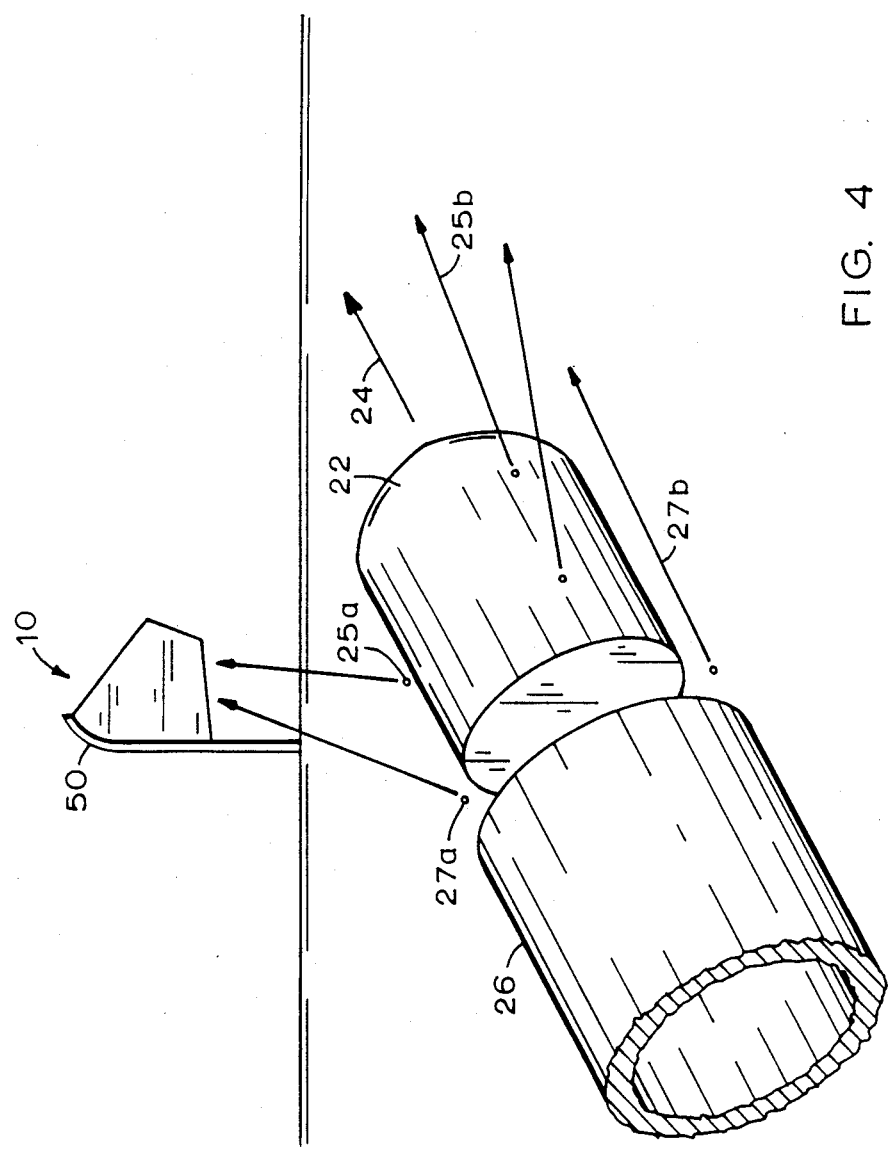
FIG. 4 is an isometric view of an embodiment adapted for large caliber firearms.

The foregoing description has been limited to a specific embodiment of this invention. It will be apparent, however, that variations and modifications may be made to the invention, with the attainment of some or all of the advantages of the invention. For example, direct adaptation of the invention as shown in FIG. 1 to testing large caliber firearms is difficult, given the required size of collector 10. FIG. 4 shows a preferred way to adapt the invention for testing a firearm such as a cannon 26 which emits a shell 22. The collector 10 is a flap shaped as a sector of a disk and held in position by a support 50 adjacent the path 24, rather than directly in the path 24. Here, the collector 10 should be positioned far enough away from the cannon 26 to prevent damage to the collector 10, but sufficiently close to collect particles emitted from the cannon 26.

Other variations will now be apparent. Therefore, it is the object of the appended claims to cover all such variations and modifications as come within the true spirit and scope of the invention.

I claim:

1. An apparatus for collecting debris emitted from a firearm, comprising:
   A. a receptacle, formed of a material sufficiently ductile so that it is easily penetrated when a projectile is fired into the apparatus; and
   B. a collecting medium, disposed on a surface of the receptacle, the collecting medium a material capable of trapping the particles exhausted from the firearm, and maintaining the particles in a matrix.

2. Apparatus as in claim 1 wherein the receptacle is formed of metal foil.

3. Apparatus as in claim 1 wherein the receptacle is disk-shaped.

4. Apparatus as in claim 1 wherein the collecting medium is soluble.

5. Apparatus as in claim 1 wherein the collecting medium is a blend of white petrolatum and paraffin wax.

6. Apparatus as in claim 1 additionally comprising:
   C. means for retaining and supporting the receptacle and medium.

7. Apparatus as in claim 6 wherein the receptacle is cemented to the retaining means at the surface opposite the surface on which the collecting medium is disposed.

8. Apparatus as in claim 6 wherein a hole is formed near the center of a bottom surface of the retaining means, the hole sufficiently large to allow a projectile to pass through when the firearm is fired.

9. Apparatus as in claim 1 additionally comprising a pair of covers adapted to enclose the receptacle and collecting medium.

10. An apparatus for collecting debris emitted from a firearm, comprising:
    A. a receptacle, formed of a metal foil in a disk shape, and sufficiently ductile so that it is easily penetrated, and moves away when a projectile is fired into the apparatus;
    B. a collecting medium, disposed on one surface of the receptacle, the collecting medium material petroleum jelly capable of trapping impinging particles exhausted from the firearm; and
    C. a container, cemented to the receptacle at the surface opposite the surface on which the collecting medium is disposed, and having a hole formed near its center, the hole sufficiently large to allow a projectile to pass through when the firearm is fired.

11. Apparatus as in claim 10 wherein the collecting medium is a blend of white petrolatum and paraffin wax in a ratio of approximately 7 to 3.

12. A method of collecting and preparing debris exhausted from a firearm, comprising the steps of
    A. placing a collecting medium in front of the barrel of the firearm;
    B. firing the firearm at the collecting medium;
    C. mixing the collecting medium together with a carrier fluid;
    D. dissolving the collecting medium in the carrier fluid;
    E. performing a particle analysis of the fluid.

13. A method as in claim 12 wherein the carrier fluid is a petroleum-based oil.

14. A method as in claim 12 wherein the collecting medium is a blend of white petrolatum and paraffin wax.

15. A method as in claim 12 wherein the medium is dissolved by mixing the medium and carrier fluid by heating.

16. A method as in claim 12 wherein the medium is dissolved into the carrier fluid by mixing them with a solvent.

17. A method as in claim 16 wherein the solvent is tetrachloroethylene.

18. A method as in claim 12 wherein the particle analysis technique is ferrography.

19. A method as in claim 12 additionally comprising:
    F. predicting firearm barrel wear by developing statistics from the results of the analysis.

* * * * *